United States Patent [19]

Maruyama et al.

[11] Patent Number: 5,352,685
[45] Date of Patent: Oct. 4, 1994

[54] THIENO[3,2-B]PYRIDINE DERIVATIVES

[75] Inventors: Akira Maruyama, Kashima; Shigeru Ogawa, Machida; Satoshi Yamazaki, Sagamihara; Akihiro Tobe, Yokohama, all of Japan

[73] Assignee: Mitsubishi Kasei Corporation, Tokyo, Japan

[21] Appl. No.: 29,551

[22] Filed: Mar. 11, 1993

[30] Foreign Application Priority Data

Mar. 12, 1992 [JP] Japan .................................. 4-053864

[51] Int. Cl.$^5$ .................... A61K 31/435; C07D 495/04
[52] U.S. Cl. .................................... 514/301; 514/183; 514/214; 540/477; 540/582; 546/114
[58] Field of Search ................ 546/114; 540/477, 582; 514/214, 301, 183

[56] References Cited

U.S. PATENT DOCUMENTS

| | | | |
|---|---|---|---|
| 4,910,193 | 3/1990 | Buchheit | 514/216 |
| 5,106,851 | 4/1992 | Turconi et al. | 514/259 |

FOREIGN PATENT DOCUMENTS

| | | |
|---|---|---|
| 0094742A2 | 11/1983 | European Pat. Off. . |
| 0200444A2 | 11/1986 | European Pat. Off. . |
| 0201165A2 | 11/1986 | European Pat. Off. . |
| 0214772 | 3/1987 | European Pat. Off. . |
| 0230718A1 | 8/1987 | European Pat. Off. . |
| 0254584A2 | 1/1988 | European Pat. Off. . |
| 0269295A1 | 6/1988 | European Pat. Off. . |
| 0307172A2 | 3/1989 | European Pat. Off. . |
| 0309423A2 | 3/1989 | European Pat. Off. . |
| 0313393A2 | 4/1989 | European Pat. Off. . |
| 0407137A2 | 1/1991 | European Pat. Off. . |
| 0458636A1 | 11/1991 | European Pat. Off. . |
| 0483836A1 | 5/1992 | European Pat. Off. . |
| 0503844A1 | 9/1992 | European Pat. Off. . |
| 0523013A2 | 1/1993 | European Pat. Off. . |
| 1-258674 | 10/1989 | Japan . |
| 3-275684 | 12/1991 | Japan . |
| 4-103583 | 4/1992 | Japan . |
| WO88/03801 | 6/1988 | PCT Int'l Appl. . |
| WO90/06309 | 6/1990 | PCT Int'l Appl. . |
| WO91/09593 | 7/1991 | PCT Int'l Appl. . |
| WO92/14733 | 9/1992 | PCT Int'l Appl. . |
| 2125398A | 3/1984 | United Kingdom . |
| 2145416A | 3/1985 | United Kingdom . |
| 2152049A | 7/1985 | United Kingdom . |
| 2169292A | 7/1986 | United Kingdom . |
| 2206788A | 1/1989 | United Kingdom . |
| 2231265A | 11/1990 | United Kingdom . |
| 2236751A | 4/1991 | United Kingdom . |

Primary Examiner—Bernard Dentz
Attorney, Agent, or Firm—Wenderoth, Lind & Ponack

[57] ABSTRACT

The thieno[3.2-b]pyridine derivative of the present invention promote the gastric emptying in male ddy mice and the gastric contraction in dogs sutured with a strain-gauge transducer. It is believed that the derivatives have the action to enhance gastric motor action and gastric emptying. Therefore, the compound of the present invention are effective for the prevention and therapeutical treatment of the symptoms caused by gastric hypanakinesis, such as heartburn, abdominal distension feeling, anorexia, unpleasant feeling on upper abdomen, abdominalgia, nausea, vomiting, etc. caused by the underlying diseases such as acute and chronic gastritis, stomach and duodenum ulcer, gastroneurosis, gastroptosis, etc. The present invention also encompasses a pharmaceutical composition containing as the effective ingredient a compound of the present invention, and a method for producing the same.

21 Claims, No Drawings

THIENO[3,2-B]PYRIDINE DERIVATIVES

FIELD OF THE INVENTION

The present invention relates to novel thieno[3,2-b]pyridine derivative useful as pharmaceutical agents. More specifically, the present invention relates to novel thieno[3,2-b]pyridine derivatives, the pharmaceutically acceptable salts thereof and the solvates thereof, effective for the prevention and therapeutical treatment of the symptoms due to gastric hypanakinesis, such as heartburn, abdominal distension feeling, anorexia, unpleasant feeling on upper abdomen, abdominalgia, nausea, vomiting, etc. caused by the underlying diseases such as acute and chronic gastritis, stomach and duodenum ulcer, gastroneurosis, gastroptosis, etc.

BACKGROUND OF THE INVENTION

So-called complaint of general malaise of gastrointestinal tract, such as heartburn, abdominal distension feeling, anorexia, unpleasant feeling on upper abdomen, nausea, vomiting, abdominalgia, etc., develop as the symptoms of diseases such as acute and chronic gastritis, stomach and duodenum ulcer, gastroneurosis, gastroptosis, etc., and the major underlying cause is the decrease in gastric emptying potency via the gastric hypanakinesis.

So as to improve gastric hypanakinesis, use has conventionally been made of 4-amino-5-chloro-N-[(2-diethylamino)ethyl]-2-methoxybenzamide [generic name; metoclopramide: see Merck Index, 11 ed., 6063(1989)], but it has been known that the agent has side effects including damage to the on extrapyramidal system or side effects on central nervous system.

Research works has been made on the pharmacological properties of a variety of substituted benzamide derivatives recently synthesized. Consequently, reports have been proposed of compounds capable of improving gastric hypanakinesis without causing the damages and side effects described above.

Known examples thereof include 4-amino-5-chloro-N-[1-[3-(4-fluorophenoxy)propyl]-3-methoxy-4-piperidinyl]-2-methoxybenzamide (generic name; cisapride: Japanese Patent Laid-open No. Sho 58-90552) and (endo)-4-amino-5-chloro-2-methoxy-N-[1-azabicyclo-(3.3.1)-non-4-yl]-benzamide hydrochloride (BRL-24924: Japanese Patent Laid-open No. Sho 62-270583).

Alternatively, it has been reported that a heterocyclic carboxylate derivative synthesized as an antagonist of the 5-HT$_3$ (serotonin 3) receptor is effective for the improvement of gastrointestinal disorders.

Known examples thereof include (endo)-8-methyl-8-azabicyclo[3.2.1]octan-3-yl indole-3-carboxylate hydrochloride (ICS205-930: Japanese Patent Laid-open No. Hei 2-237920) and (endo)-N-[8-aza-8-methylbicyclo[3.2.1]octan-3-yl]-1-methylquinolin-4-one-3-carboxamide (GB2236751A).

However, expectation has been toward the development of a novel compound capable of further improving gastric hypanakinesis.

SUMMARY OF THE INVENTION

Therefore, the present inventors have made investigations extensively so as to find a heterocyclic compound having a novel structure and capable of greatly enhancing gastric motor function. The, the inventors have found that the objective can be achieved with a specific thieno[3,2-b]pyridine derivative. Thus, the inventors have achieved the present invention.

That is, the present invention is summarized as a thieno[3,2-b]pyridine derivative represented by formula (I):

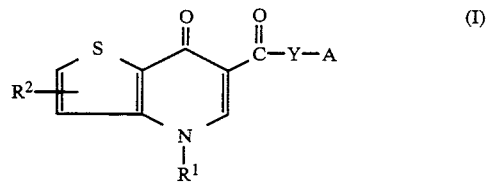

(wherein Y represents —O— or

(wherein $R^3$ represents hydrogen atom or a $C_1$–$C_6$ alkyl group); $R^1$ represents hydrogen atom, a $C_1$–$C_6$ alkyl group, a $C_2$–$C_6$ alkenyl group, a $C_2$–$C_6$ alkynyl group, a $C_3$–$C_8$ cycloalkyl group, a $C_6$–$C_{12}$ aryl group or a $C_7$–$C_{18}$ aralkyl group; $R^2$ represents hydrogen atom, a $C_1$–$C_6$ alkyl group, halogen atom, hydroxyl group, a $C_1$–$C_6$ alkoxyl group, amino group, a $C_1$–$C_6$ alkylamino group, nitro group, mercapto group or a $C_1$–$C_6$ alkylthio group; and A is represented by

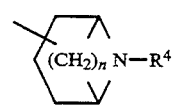

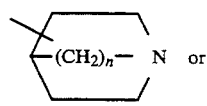

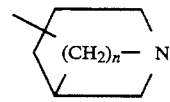

(wherein n is an integer of 1 to 4; $R^4$ represents hydrogen atom, a $C_1$–$C_6$ alkyl group, a $C_3$–$C_8$ cycloalkyl group or a $C_7$–$C_{18}$ aralkyl group): pharmaceutically acceptable salts thereof; N-oxide derivatives thereof and solvates thereof; and the use and method for producing the same.

DETAILED DESCRIPTION OF THE INVENTION

For detailed description of the invention, the compound of the present invention are represented by formula (I):

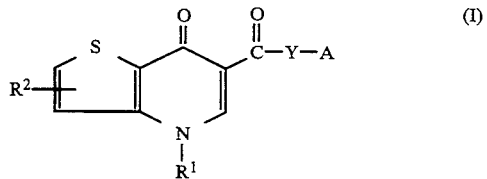

wherein Y represents —O— or

(wherein $R^3$ represents hydrogen atom or a $C_1$-$C_6$ alkyl group, such as methyl group, propyl group, hexyl group, etc.); $R^1$ represents hydrogen atom, a $C_1$-$C_6$ alkyl group, such as methyl group, propyl group, hexyl group, etc., a $C_2$-$C_6$ alkenyl group, such as vinyl group, butenyl group, hexenyl group, etc., having one or two double bonds, a $C_2$-$C_6$ alkynyl group, such as ethynyl group, butynyl group, hexynyl group, etc., having one or two triple bonds, a $C_3$-$C_8$ cycloalkyl group, such as cyclopropyl group, cyclohexyl group, cyclooctyl group, etc., a $C_6$-$C_{12}$ aryl group, such as phenyl group, naphthyl group, etc., which may or may not have substituents, or a $C_7$-$C_{18}$ aralkyl group, such as a $C_1$-$C_6$ alkyl group having a $C_6$-$C_{12}$ aryl group (phenyl group, naphtyl group, etc.), such as benzyl group, phenethyl group, etc.; $R^2$ represents hydrogen atom, a $C_1$-$C_6$ alkyl group, such as methyl group, propyl group, hexyl group, etc., halogen atom (fluorine atom, chlorine atom, bromine atom, iodine atom, etc.), hydroxyl group, a $C_1$-$C_6$ alkoxyl group, such as methoxy group, propoxy group, hexyloxy group, etc., amino group, a $C_1$-$C_6$ alkylamino group, such as methylamino group, propylamino group, hexylamino group, etc., nitro group, mercapto group or a $C_1$-$C_6$ alkylthio group, such as methylthio group, propylthio group, hexylthio group, etc.; and A is represented by

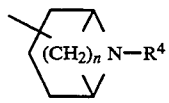

(II)

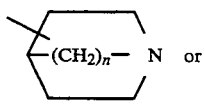

(III)

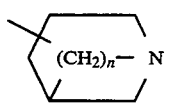

(IV)

{wherein n is an integer of 1 to 4; $R^4$ represents hydrogen atom, a $C_1$-$C_6$ alkyl group, such as methyl group, propyl group, hexyl group, etc., a $C_3$-$C_8$ cycloalkyl group such as cyclopropyl group, cyclohexyl group, cyclooctyl group, etc., or a $C_7$-$C_{18}$ aralkyl group, such as a $C_1$-$C_6$ alkyl group (methyl group, propyl group, hexyl group, etc.) having a $C_6$-$C_{12}$ aryl group (phenyl group, naphtyl group, etc.), such as benzyl group, phenethyl group, etc.}; the pharmaceutically acceptable salts thereof; the N-oxide derivatives and the solvates thereof.

The pharmaceutically acceptable salts of the compounds represented by the above general formula (i) include acid addition salts and tetra-ammonium salts thereof. The acid addition salts include inorganic salts such as hydrochloride, hydrobromide, sulfate, phosphate and the like; and organic salts such as oxalate, maleate, fumarate, lactate, maliate, citrate, tartrate, benzoate, methanesulfonate and the like.

The tetra-ammonium salts include tetraammonium salts of, for example, a lower alkyl halogenide such as methyl iodide, methyl bromide, ethyl iodide, and ethyl bromide; a lower alkyl sulfonate such as methyl methanesulfonate and ethyl methanesulfonate; a lower alkyl arylsulfonate such as methyl p-toluenesulfonate.

The N-oxide derivatives at A of the compounds of the general formula (I) are also encompassed within the compounds of the present invention.

The compound of the above general formula (I), the pharmaceutically acceptable salts thereof or the N-oxide derivatives thereof may be present as solvates, and these solvates are also included in the compound of the present invention.

Furthermore, if A of the compound of the above general formula (I) has an asymmetric carbon atom, optical isomers, mixtures thereof and racemic modifications thereof are also included in the compound of the present invention.

If $R^1$ is hydrogen atom in the compound of the present invention, the tautomer represented by the following general formula (IX) exists, which is also included in the compound of the present invention.

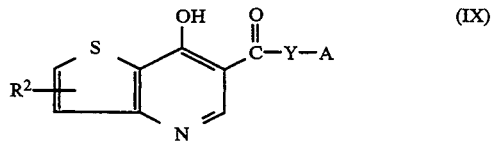

wherein $R^2$ is as defined in the above general formula (I).)

In the above general formula (I), Y preferably represents —O— or

and $R^1$ is preferably hydrogen atom, a $C_1$-$C_6$ alkyl group, and a $C_6$-$C_{12}$ aryl group; $R^2$ is preferably hydrogen atom, a $C_1$-$C_6$ alkyl group and halogen atom; and A preferably has n as an integer of 2 to 3. In the above general formula (II), $R^4$ preferably is methyl group.

Preferable examples of the compounds represented by the general formula (I) in accordance with the present invention include a compound represented by the general formula (Ia):

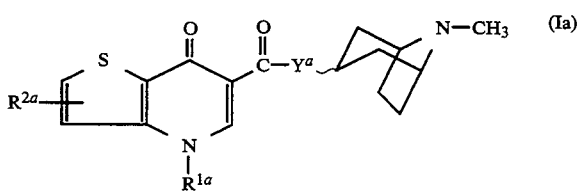

(In the above general formula (Ia), $Y^a$ represents —O— or

$R^{1a}$ represents hydrogen atom, a $C_1$-$C_6$ alkyl group or a $C_6$-$C_{12}$ aryl group; $R^{2a}$ represents hydrogen atom, a $C_1$-$C_6$ alkyl group or halogen atom); the acid addition salts thereof, the N-oxide derivatives thereof and the solvates thereof; a compound represented by the general formula (Ib):

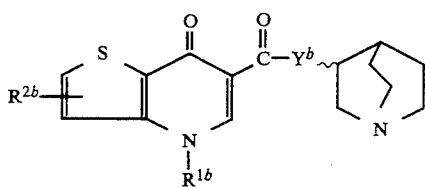

(Ib)

(In the above general formula (Ib), $Y^b$ represents —O— or $$-\overset{H}{\underset{|}{N}}-$$

$R^{1b}$ represents hydrogen atom, a $C_1$–$C_6$ alkyl group or a $C_6$–$C_{12}$ aryl group; $R^{2b}$ represents hydrogen atom, a $C_1$–$C_6$ alkyl group or halogen atom); the optical isomers thereof, the mixtures or racemic modifications thereof, the acid addition salts thereof, the N-oxide derivatives thereof or the solvates thereof; and a compound represented by the general formula (Ic):

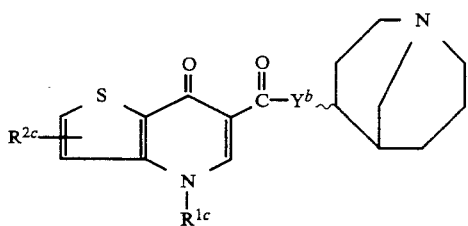

(Ic)

(In the above general formula (Ic), $Y^c$ represents —O— or $$-\overset{H}{\underset{|}{N}}-$$

$R^{1c}$ represents hydrogen atoms, a $C_1$–$C_6$ alkyl group or a $C_6$–$C_{12}$ aryl group; $R^{2c}$ represents hydrogen atom, a $C_1$–$C_6$ alkyl group or halogen atom); the optical isomers thereof, the mixtures or racemic modifications thereof, the acid addition salts thereof, the N-oxide derivatives thereof or the solvates thereof.

Particularly preferable examples thereof are shown in the following Tables 1 to 3 (the acid addition salts thereof are also preferable compounds), but within the scope of the invention, the present invention is not limited to the following compounds and the acid addition salts thereof.

TABLE 1

| Compound No. | $R^{1a}$ | $R^{1b}$ | $Y^a$ | Conformation |
|---|---|---|---|---|
| 1 | —H | —H | —NH— | endo |
| 2 | —H | —H | —O— | endo |
| 3 | —H | —H | —NH— | exo |

TABLE 1-continued

| Compound No. | $R^{1a}$ | $R^{1b}$ | $Y^a$ | Conformation |
|---|---|---|---|---|
| 4 | —CH$_3$ | —H | —NH— | endo |
| 5 | —H | 3-CH$_3$ | —NH— | endo |
| 6 | —H | 3-Br | —NH— | endo |

TABLE 2

| Compound No. | $R^{1b}$ | $R^{2b}$ | $Y^b$ |
|---|---|---|---|
| 7 | —H | —H | —NH— |
| 8 | —H | —H | —O— |
| 9 | —CH$_3$ | —H | —NH— |
| 10 | —H | 3-CH$_3$ | —NH— |
| 11 | —H | 2-CH$_3$ | —NH— |
| 12 | —H | 3-Br | —NH— |
| 13* | —H | —H | —NH— |
| 14* | —CH$_3$ | —H | —NH— |

(The symbol "*" represents N-oxide derivative; "13*" represents N-(1-azabicyclo[2.2.2]oct-1-oxide-3-yl)-7-hydroxythieno[3.2-b]pyridine-6-carboxamide; and "14*" represents N-(1-azabicyclo[2.2.2]oct-1-oxide-3-yl)-4,7-dihydro-4-methyl-7-oxothieno[3.2-b]pyridine-6-carboxamide.)

TABLE 3

| Compound No. | $R^{1c}$ | $R^{2c}$ | $Y^c$ |
|---|---|---|---|
| 15 | —H | —H | —NH— |

The compounds represented by the above general formula (I) in accordance with the present invention can be produced by reacting a carboxylic acid represented by the following general formula (V):

(V)

(In the above general formula (V), $R^1$ represents hydrogen atom, a $C_1-C_6$ alkyl group, a $C_2-C_6$ alkenyl group, a $C_2-C_6$ alkynyl group, a $C_3-C_8$ cycloalkyl group, a $C_6-C_{12}$ aryl group or a $C_7-C_{18}$ aralkyl group; $R^2$ represents hydrogen atom, a $C_1-C_6$ alkyl group, halogen atom, hydroxyl group, a $C_1-C_6$ alkoxy group, amino group, a $C_1-C_6$ alkylamino group, nitro group, mercapto group or a $C_1-C_6$ alkylthio group), or a reactive derivative thereof with the amine or alcohol represented by the following general formula (VI), (VII) or (VIII):

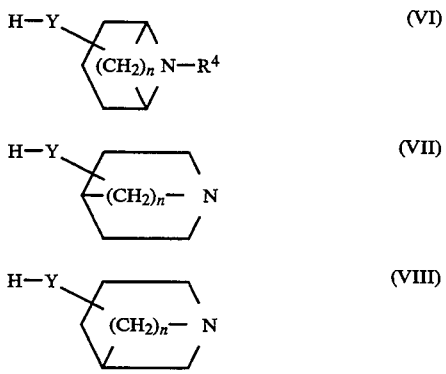

[In the above formula, Y represents —O— or

(wherein $R^3$ represents hydrogen atom or a $C_1-C_6$ alkyl group); n represents an integer of 1 to 4; $R^4$ represents hydrogen atom, a $C_1-C_6$ alkyl group, a $C_3-C_8$ cycloalkyl group or a $C_7-C_{18}$ aralkyl group.]; or the alkaline metal salt thereof.

A compound having Y represented by

in the above general formula (I) can be produced, for example, by the following methods.

(1-1) The compound can be produced by reacting the carboxyl group of the compound represented by the general formula (V) with N, N'-carbonyl diimidazole, N-hydroxysuccinimide, N, N'-dicyclohexyl carbodiimide, pentachlorophenol, etc., thereby producing an appropriate acid derivative with enriched reactivity, and reacting in a solvent the amine represented by the above general formula (VI), (VII) or (VIII) with the resulting acid derivative.

As such solvent, there may be included dichloromethane, chloroform, benzene, toluene, tetrahydrofuran, N, N-dimethylformamide, dimethylsulfoxide, etc. The reaction temperature is selected from a range of 0° to 200° C., preferably 10° to 130° C., and the duration of the reaction is 5 minutes to 20 hours, preferably 30 minutes to 10 hours.

(1-2) The compound can be produced by reacting the compound represented by the above general formula (V) with oxalyl chloride, thionyl chloride, phosphorous trichloride, phosphorous oentachloride, phosphorous oxychloride, phosphorous tribromide, etc. at 0° to 100° C. for about 5 minutes to 2 hours, and reacting the amine represented by the general formula (VI), (VII) or (VIII) with the resulting acid halide, preferably acid chloride.

As such solvent, there may be included dichloromethane, chloroform, benzene, toluene, tetrahydrofuran, N, N-dimethylformamide, etc., in the presence of tertiary amines such as triethylamine and pyridine if necessary, which amines may be used as solvents, or in the presence of alkali metal salts such as potassium carbonate and sodium carbonate. The reaction temperature is selected from a range of —30° to 100° C., preferably —10° to 80° C., and the duration of the reaction is 5 hours or less, preferably 5 minutes to 2 hours.

A compound having Y represented by —O— in the above general formula (I) can be produced, for example, by the following methods.

(2-1) The compound can be produced by reacting in a solvent the acid derivative with enriched reactivity of the general formula (V) described above in (1-1) with an alkali metal salt such as lithium salt and sodium salt of the alcohol represented by the above general formula (VI), (VII) or (VIII) or of an alcohol produced by reacting the alcohol represented by the above general formula (VI), (VII) or (VIII) with n-butyllithium in a solvent of tetrahydrofuran, or by reacting the alcohol with sodium hydride in a solvent of N, N-dimethylformamide.

As such solvent, there may be included tetrahydrofuran, dioxane, diethylether, N, N-dimethylformamide, etc. The reaction temperature is selected from a range of 0° to 200° C., preferably 10° to 120° C., and the duration of the reaction is about 30 minutes to 10 hours.

(2-2) The compound can be produced by reacting in a solvent the highly reactive acid halide, preferably acid chloride of the compound of the general formula (V) described above in (1-2) with the alcohol represented by the above general formula (VI), (VII) or (VIII) or the alkali metal salt thereof.

As such solvent, preference is given to tetrahydrofuran, dimethoxyethane, dioxane, etc. The reaction temperature is selected from a range of —20° to 100° C., preferably 0° to 70° C., and the duration of the reaction is 5 hours or less, preferably about 5 minutes to 2 hours.

It is believed that in the above reaction, the steric conformation of the amine or alcohol represented by the above general formula (VI), (VII) or (VIII) is retained as it is. If A has an asymmetric carbon atom in the above general formula (I), therefore, the optical isomer thereof can be produced by the reaction of the optical isomer of the amine or alcohol represented by the above general formula (VI), (VII) or (VIII). If necessary, a mixture of the optical isomers or racemic modifications of the amine or alcohol is reacted prior to a general optical resolution method [comprising introducing the diastereomer salt thereof with a general optically active acid (tartrate, etc.) prior to optical resolution] to produce the compound.

If A has an endo or oxo steric conformation in the above general formula (I), the steric isomer thereof can be produced by the reaction of the corresponding steric isomer of the amine or alcohol represented by the above general formula (VI), (VII) or (VIII). If necessary, the reaction of a mixture of the endo and exo isomers of the amine or alcohol is done prior to a routine method such as chromatography or recrystallization, to separate an endo or exo isomer.

The compound represented by the above general formula (I) thus obtained can form an acid addition salt and a tetra-ammonium salt by various conventionally known various methods.

By oxidizing in a solvent the compound represented by the general formula (I) with hydrogen peroxide, m-chloroperbenzoic acid, peracetic acid, monopermaleic acid, monoperphthalic acid, etc., the N-oxide derivative can be produced.

As such solvent, preference is given to chloroform, dichloromethane, methanol, ethanol, diethylether, acetic acid, etc., and the reaction is at 0° to 100° C., preferably 20° to 60° C., for 10 minutes to one week.

Alternatively, the N-oxide derivative of the compound represented by the above general formula (I) can be produced by introducing the amine or alcohol represented by the above general formula (VI), (VII) or (VIII) into the N-oxide derivative thereof by the same procedures, and effecting the condensation reaction of the resulting N-oxide derivative, with the compound represented by the general formula (V) or the reactive derivative thereof, by the same procedures as in (1-1), (1-2), (2-1) and (2-2) described above.

Furthermore, the acid addition salt of the compound represented by the general formula (I) is recrystallized in an aqueous solution which may or may not contain, for example, alcohols (methanol, ethanol, etc.), ketones (acetone, etc.), ethers (tetrahydrofuran, dioxane, etc.) to aid the solubilization of the compound, to produce the solvate of the desired compound.

The preparation containing as the effective compound one or two or more of the compound represented by the above general formula (I), the pharmaceutically acceptable salt thereof, the N-oxide derivative thereof or the solvate thereof, can be mixed with a routine formulating carrier for preparation into tablets, capsules, fine granules, powders, pills, troches, liquids, injections, suppositories, ointments, patches, etc. The preparation is then administered orally or parenterally (including sublingual administration).

The tablets and capsules for oral dose are provided in a form of unit dose, containing routine carriers such as binders, fillers, dilution agents, tableting agents, lubricating-agents, degrading agents, coloring agents, flavoring agents and emollients. The tablet can be coated, for example, with an enteric coating according to a known method in this art.

The fillers appropriate for use include cellulose, mannitol, lactose and other similar pharmaceutical agents. Appropriate such degrading agents include carbohydrate, polyvinylpyrrolidone, and carbohydrate derivatives, for example, sodium carbohydrate glycolate and the like. Appropriate such emollients include, for example, sodium laurylsulfate. Such oral liquids are provided, for example, in the form of aqueous or oily suspensions, solutions, emulsions, syrups or elixirs or in the form of a dry product which can be resolubilized in water or an appropriate solvent prior to use. Such liquids may contain general additives, for example, precipitation preventive agents such as sorbitol, syrup, methyl cellulose, gelatin, hydroxyethyl cellulose, carboxymethyl cellulose, aluminium stearate gel or hydrogenated edible fats; emulsifiers such as lecithin, sorbitan monooleate, gum arabic; non-aqueous solvents such as almond oil, purified coconut oil, liquid-like esters (for example, glycerin ester), propylene glycol and ethyl alcohol (including edible oils); preservatives such as the methyl ester, ethyl ester or propyl ester of p-hydroxybenzoic acid or sorbic acid; and general flavoring agents and coloring agents if necessary.

The oral composition is produced by conventional methods such as mixing, filling or tableting. By using a compounding procedure in repetition, an active agent may be distributed in these compositions containing a great amount of fillers.

For parenteral dose, a formulation in liquid unit dose, containing the compound of the present invention and a sterilized liquid, may be produced. The compound may be suspended or solubilized, depending on the type of the solvent and the concentration. Parenteral liquid may be produced by dissolving the compound in a solvent followed by sterilization and filtering, which is then filled in an appropriate vial or ampoule for sealing. So as to increase the stability, the composition may be lyophilized prior to filling into a vial, followed by dehydration in vacuum for use.

Parenteral suspension may be produced by substantially the same manner as in the parenteral liquid, but the compound may be suspended in a solvent instead of being dissolved therein, which is then exposed to ethylene oxide for sterilization. Furthermore, the sterilized suspension is then suspended in a sterilized solvent. In order that the compound of the present invention may be distributed uniformly, a surfactant, an emollient and the like may be added, if necessary.

The clinical dose of the compound of the present invention may appropriately be determined in light of the symptoms, body weight, age, sex of the patient to be administered, but per adult per day, the dose may be 0.05 to 100 mg for oral administration; and 0.01 to 20 mg for intravenous administration. The dose preferably may be divided one to several times per day.

PREFERRED EMBODIMENTS OF THE INVENTION

The present invention will now be explained in detail in examples, but within the scope of the invention, the present invention is not limited to them.

EXAMPLE 1

Synthesis of N-(1-azabicyclo[2.2.2]oct-3-yl)-7-hydroxythieno[3.2-b]pyridine-6-carboxamide (Compound No.7 in Table 2 and its tautomer) and hydrochloride thereof (a) To 50 ml of N, N-dimethylformamide were added 4.98 g of 7-hydroxythieno[3.2-b]pyridine-6-carboxylic acid and 4.55 g of N, N'-carbonyl diimidazole, followed by agitation under heating at 70° C. for 1 hour. To the resulting solution was added 4.19 g of 1-azabicyclo[2.2.-2]oct-3-yl amine dissolved in 10 ml of N, N-dimethylformamide, followed by agitation under heating at 70° C. for 2.5 hours. After cooling, the deposited crystal was filtered and washed in hexane and ethyl ether, which was then recrystallized in a mixed solvent of ethanol and water to obtain 4.21 g of the objective compound.

Melting point: >300° C.

$^1$HNMR (DMSO-$d_6$, $\delta$ppm): 1.40–1.95 (5H, m), 2.50–2.62 (1H, m), 2.70–2.95 (4H, m), 3.25–3.40 (1H, m), 3.95–4.10 (1H, m), 7.31 (1H, d), 8.01 (1H, d), 8.64 (1H, s), 10.79 (1H, d), (b) The objective compound (4.21 g) obtained in (a) was dissolved in a mixed solvent of 100 ml of ethanol and 150 ml of chloroform, followed by addition of 13.9 ml of 1N hydrogen chloride in ethanol in solution under ice cooling. The resulting solution was concentrated under reduced pressure to a final volume of 25 ml, and the deposited crystal was filtered to obtain 4.44 g of the objective compound.

Melting point: 290°–295° C.

$^1$HNMR (DMSO-$d_6$, δppm): 1.75–2.10 (4H, m), 2.10–2.25 (1H, m), 2.95–3.10 (1H, m), 3.10–3.60 (4H, m), 3.60–3.75 (1H, m), 4.25–4.40 (1H, m), 7.40 (1H, d), 8.15 (1H, d), 8.66 (1H, s), 10.66 (1H, d),

EXAMPLE 2

Synthesis of R-N-(1-azabicyclo[2.2.2]oct-3-yl)-7-hydroxythieno[3.2-b]pyridine-6-carboxamide (Compound No.7 in Table 2 and its tautomer) and hydrochloride thereof (a) To 490 ml of N, N-dimethylformamide were added 47.7 g of 7-hydroxythieno[3.2-b]pyridine-6-carboxylic acid and 43.5 g of N, N'-carbonyl diimidazole, followed by agitation under heating at 70° C. for 1 hour. To the resulting solution was added 37.0 g of R-1-azabicyclo[2.2.2]oct-3-yl amine dissolved in 100 ml of N, N-dimethylformamide, followed by agitation under heating at 65° C. for 2 hours. After distilling off the solvent under reduced pressure, the residue was subjected to silica gel column chromatography (eluent; chloroform: methanol: 28% aqueous ammonia=85:15:0.3). The eluted crystal was processed with 2.5 g of active charcoal (solvent; chloroform: methanol=1:1), followed by recrystallization in a mixed solvent of ethanol and water and further washing in 20 ml of methanol to obtain 52.01 g of the objective compound.

Melting point: 280°–290° C.

$^1$HNMR (DMSO-$d_6$, δppm): 1.40–1.95 (5H, m), 2.50–2.62 (1H, m), 2.70–3.00 (4H, m), 3.25–3.40 (1H, m), 3.95–4.10 (1H, m), 7.33 (1H, d), 8.04 (1H, d), 8.64 (1H, s), 10.76 (1H, d), (b) The objective compound (51.33 g) obtained in (a) was dissolved in a mixed solvent of 450 ml of methanol and 390 ml of chloroform, followed by addition of 169.2 ml of 1N hydrogen chloride in ethanol in solution under ice cooling. After distilling off the solvent under reduced pressure followed by addition of 513 ml of ethanol, the resulting solution was refluxed under heating for 20 minutes. After cooling, the crystal was filtered to obtain 51.09 g of the objective compound.

Melting point: >300° C.

$[α]^{20}_D$ = −17.8° (C=1, H$_2$O), $^1$HNMR (DMSO-$d_6$, δppm): 1.75–2.10 (4H, m), 2.10–2.25 (1H, m), 2.95–3.10 (1H, m), 3.10–3.60 (4H, m), 3.60–3.75 (1H, m), 4.25–4.40 (1H, m), 7.41 (1H, d), 8.16 (1H, d), 8.66 (1H, s), 10.66 (1H, d),

EXAMPLE 3

Synthesis of S-N-(1-azabicyclo[2.2.2]oct-3-yl)-7-hydroxythieno[3.2-b]pyridine-6-carboxamide (Compound No.7 in Table 2 and its tautomer) and hydrochloride thereof (a) To 50 ml of N, N-dimethylformamide were added 5.80 g of 7-hydroxythieno[3.2-b]pyridine-6-carboxylic acid and 5.30 g of N, N'-carbonyl diimidazole, followed by agitation under heating at 70° C. for 1 hour. To the resulting solution was added 4.87 g of S-1-azabicyclo[2.2.2]oct-3-yl amine dissolved in 20 ml of N, N-dimethylformamide, followed by agitation under heating at 70° to 75° C. for 1 hour. After distilling off the solvent under reduced pressure, the residue was subjected to silica gel column chromatography (eluent; chloroform:methanol:28% aqueous ammonia=85:15:0.3). The eluted crystal was recrystallized in a mixed solvent of ethanol and water and further washed in methanol to obtain 6.40 g of the objective compound.

Melting point: 294–298° C.

$^1$HNMR (DMSO-$d_6$, δppm): 1.40–1.95 (5H, m), 2.50–2.63 (1H, m), 2.70–3.00 (4H, m), 3.25–3.40 (1H, m), 3.95–4.10 (1H, m), 7.32 (1H, d), 8.02 (1H, d), 8.64 (1H, s), 10.77 (1H, d), (b) The objective compound (6.30 g) obtained in (a) was dissolved in a mixed solvent of 35 ml of methanol and 70 ml of chloroform, followed by addition of 20.8 ml of 1N hydrogen chloride in ethanol in solution under ice cooling. After distilling off the solvent under reduced pressure and adding 50 ml of ethanol, reflux under heating was effected for 10 minutes. After cooling, the crystal was filtered to obtain 6.54 g of the objective compound.

Melting point: >300

$[α]^{20}_D$ = +17.6° (C=1, H$_2$O), $^1$HNMR (DMSO-$d_6$, δppm): 1.75–2.10 (4H, m), 2.10–2.25 (1H, m), 3.00–3.15 (1H, m), 3.15–3.60 (4H, m), 3.60–3.75 (1H, m), 4.25–4.40 (1H, m), 7.40 (1H, d), 8.16 (1H, d), 8.67 (1H, s), 10.67 (1H, d),

EXAMPLE 4

Synthesis of 1-azabicyclo[2.2.2]oct-3-yl 7-hydroxythieno[3.2-b]pyridine-6-carboxylate (Compound No.8 and tautomer in Table 2) and hydrochloride thereof (a) To 16 ml of N, N-dimethylformamide were added 0.80 g of 7-hydroxythieno[3.2-b]pyridine-6-carboxylic acid and 0.73 g of N, N'-carbonyl diimidazole, followed by agitation under heating at 60° C. for 1 hour. To the resulting solution was added 0.63 g of 1-azabicyclo[2.2.2]oct-3-yl alcohol dissolved in 10 ml of N, N-dimethylformamide, followed by agitation under heating at 80° C. for 3 hours. After cooling, the deposited crystal was filtered and washed in chloroform, to obtain 0.88 g of the separated objective compound.

$^1$HNMR (CDCl$_3$-CD$_3$OD, δppm): 1.50–1.90 (3H, m), 2.10–2.30 (2H, m), 2.70–3.15 (5H, m), 3.30–3.45 (1H, m), 5.05–5.15 (1H, m), 7.27 (1H, d), 7.84 (1H, d), 8.58 (1H, s), (b) The objective compound (0.88 g) obtained in (a) was dissolved in a mixed solvent of 90 ml of chloroform and 70 ml of methanol, followed by addition of 289 ml of 1N hydrogen chloride in ethanol in solution under ice cooling. After distilling off the solvent under reduced pressure, 0.93 g of the objective compound was obtained.

Melting point: >300

$^1$HNMR (DMSO-$d_6$, δppm): 1.7–2.05 (3H, m), 2.15–2.40 (2H, m), 3.05–3.55 (5H, m), 3.60–3.75 (1H, m), 5.05–5.20 (1H, m), 7.34 (1H, d), 8.06 (1H, d), 8.59 (1H, s),

EXAMPLE 5

Synthesis of (endo)-N-(8-methyl-8-azabicyclo[3.2.1]oct-3-yl)-7-hydroxythieno[3.2-b]pyridine-6-carboxamide (Compound No.1 in Table 1 and its tautomer) and hydrochloride thereof (a) To 12 ml of N, N-dimethylformamide were added 0.80 g of 7-hydroxythieno[3.2-b]pyridine-6-carboxylic acid and 0.95 g of N, N'-carbonyl diimidazole, followed by agitation under heating at 60° C. for 1 hour. To the resulting solution was added 0.75 g of (endo)-8-methyl-8-azabicyclo[3.2.1]oct-3-yl amine dissolved in 2 ml of N, N-dimethylformamide, followed by agitation under heating at 60° C. for 5 hours. After distilling off the solvent under reduced pressure, the residue was subjected to silica gel column chromatography (eluent; chloroform:methanol:28% aqueous ammonia=90:10:0.3) for purification, to obtain 0.52 g of the objective compound.

Melting point: 270–280° C. (decomposed).

$^1$HNMR (DMSO-d$_6$, δppm): 1.60–1.78 (2H, m), 2.05–2.30 (6H, m), 2.38 (3H, s), 3.25–3.45 (2H, bs), 4.05–4.20 (1H, m), 7.31 (1H, d), 8.01 (1H, d), 8.64 (1H, s), 10.96 (1H, d), (b) The objective compound (0.52 g) obtained in (a) was dissolved in a mixed solvent of 8 ml of ethanol and 8 ml of chloroform, followed by addition of 1.64 ml of 1N hydrogen chloride in ethanol in solution under ice cooling. After distilling off the solvent under reduced pressure, 0.45 of the objective compound was obtained.

Melting point: 280°–286° C. (decomposed).

$^1$HNMR (DMSO-d$_6$, δppm): 1.90–2.10 ( 2H, m), 2.20–2.95 (9H, m), 3.70–4.00 (2H, m), 4.10–4.35 (1H, m), 7.45 (1H, d), 8.18 (1H, d), 8.65 (1H, s), 10.70–11.00 (2H, m), 13.70 (1H, bs),

EXAMPLE 6

Synthesis of
(endo)-8-methyl-8-azabicyclo[3.2.1]oct-3-yl 7-hydroxythieno[3.2-b]pyridine-6-carboxylate (Compound No.2 in Table 1 and its tautomer) and hydrochloride thereof (a) (Endo)-8-methyl-8-azabicyclo[3.2.1]oct-3-yl alcohol (tropine; 0.85 g) was dissolved in 4 ml of anhydrous tetrahydrofuran, followed by dropwise addition of 3.17 ml of a solution of 15 % butyllithium in hexane below 0° C. After agitation at room temperature for 30 minutes, a tropin solution in lithium salt was prepared. To 14 ml of N, N-dimethylformamide were added 0.90 g of 7-hydroxythieno[3.2-b]pyridine-6-carboxylic acid and 0.82 g of N, N'-carbonyl diimidazole, followed by agitation under heating at 65° C. for 1 hour. To the resulting solution was added the tropin solution in lithium salt, followed by agitation under heating at 60 ° C. for 1 hour. After drying under reduced pressure, the resulting residue was subjected to silica gel column chromatography (eluent; chloroform:methanol:28% aqueous ammonia=85:15:0.3) for purification. The resulting crystal was washed in methanol to obtain 0.38 g of the objective compound.

$^1$HNMR (DMSO-d$_6$, δppm): 1.65–1.78 (2H, m), 1.90–2.20 (6H, m), 2.23 (3H, s), 3.05–3.20 (2H, m), 5.00–5.10 (1H, m), 7.25 (1H, d), 7.81 (1H, d), 8.63 (1H, s), (b) The objective compound (0.38 g) obtained in (a) was dissolved in 40 ml of ethanol and 50 ml of chloroform, followed by addition of 1.16 ml of the solution of 1N hydrogen chloride in ethanol under ice cooling. After distilling off the solvent under reduced pressure, 0.41 g of the objective compound was obtained.

Melting point: 279°–282° C. (decomposed).

$^1$HNMR (DMSO-d$_6$, δppm): 1.85–1.95 (2H, m), 2.00–2.20 (2H, m), 2.30–2.50 (4H, m), 2.52 (3H, s), 3.57 (2H, bs), 5.05–5.15 (1H, m), 7.29 (1H, d), 7,98 (1H, d), 8.52 (1H, s),

EXAMPLE 7

Synthesis of
(exo)-N-(8-methyl-8-azabicyclo[3.2.1]oct-3-yl)-7-hydroxythieno[3.2-b]pyridine-6-carboxamide (Compound No.3 in Table 1 and its tautomer) and hydrochloride thereof (a) To 12 ml of N, N-dimethylformamide were added 0.80 g of 7-hydroxythieno[3.2-b]pyridine-6-carboxylic acid and 0.73 g of N, N'-carbonyl diimidazole, followed by agitation under heating at 60° C. for 30 minutes. To the resulting solution was added 0.69 g of (exo)-8-methyl-8-azabicyclo[3.2.1]oct-3-yl amine dissolved in 2 ml of N, N-dimethylformamide, followed by agitation under heating at 60° C. for 1 hour. After distilling off the solvent under reduced pressure, the residue was subjected to silica gel column chromatography (eluent; chloroform:methanol: 28% aqueous ammonia=85:15:0.3) for purification, to obtain 0.75 g of the objective compound.

$^1$HNMR ( DMSO-d$_6$, δppm): 1.50–1.75 (45, m), 1.75–1.92(2H, m), 2.00–2.15 (2H, m), 2.34 (3H, s), 3.25–3.40 (2H, bs), 4.05–4.25 (1H, m), 7.29 (1H, d), 7.98 (1H, d), 8.61 (1H, s), 10.24 (1H, d), (b) The objective compound (0.75 g) obtained in (a) was dissolved in 60 ml of ethanol, followed by addition of 2.36 ml of the solution of 1N hydrogen chloride in ethanol. After distilling off the solvent, the objective compound (0.76 g) was obtained.

Melting point: >300° C.

$^1$HNMR (CD$_3$OD-D$_2$O, δppm): 1.95–2.10 (2H, m), 2.10–2.30 (6H, m), 2.83 (3H, s), 3.90–4.10 (2H, bs), 4.38–4.58 (1H, m), 7.42 (1H, d), 8.09 (1H, d), 8.74 (1H, s)

EXAMPLE 8

Synthesis of
(endo)-N-(1-azabicyclo[3.3.1]non-4-yl)-7-hydroxythieno[3.2-b]pyridine-6-carboxamide (Compound No.15 in Table 3 and its tautomer) and hydrochloride thereof (a) To 50 ml of N, N-dimethylformamide were added 3.23 g of 7-hydroxythieno[3.2-b]pyridine-6-carboxylic acid and 2.76 g of N, N'-carbonyl diimidazole, followed by agitation under heating at 65° C. for 1 hour. To the resulting solution was added 2.55 g of (endo)-1-azabicyclo[3.3.1]-non-4-yl amine dissolved in 7 ml of N, N-dimethylformamide, followed by agitation under heating at 65° C. for 1 hour. After distilling off the solvent under reduced pressure, the residue was subjected to silica gel column chromatography (eluent; chloroform:methanol:28% aqueous ammonia=85:15:0.3) for purification, and the resulting crystal was purified by alumina column chromatography (eluent; chloroform:methanol=95:5) to obtain 0.39 g of the objective compound.

$^1$HNMR (DMSO-d$_6$, δppm): 1.40–1.58 (1H, m), 1.70–2.05 (6H, m), 2.90–3.25 (6H, m), 4.20–4.40 (1H, m), 7.30 (1H, d), 8.00 (1H, d), 8.65 (1H, s), 10.60 (1H, d), (b) The objective compound (0.37 g) obtained in (a) was dissolved in ethanol, followed by addition of 1.17 ml of the solution of 1N hydrogen chloride in ethanol. After distilling off the solvent, the objective compound (0.41 g) was obtained.

Melting point: >300° C.

¹HNMR (DMSO-d₆, δppm): 1.70–2.00 (3H, 2.00–2.30 (4H, m), 3.20–3.55 (6H, m), 4.35–4.55 (1H, m), 7.38 (1H, d), 8.14 (1H, d), 8.67 (1H, s), 10.45 (1H, d)

EXAMPLE 9

Synthesis of N-(1-azabicyclo[2.2.2]oct-3-yl)-4,7-dihydro-4-methyl-7-oxothieno[3.2-b]pyridine-6-carboxamide (Compound No.9 in Table 2) and hydrochloride thereof (a) To 20 ml of N, N-dimethylformamide were added 0.70 g of 4,7-dihydro-4-methyl-7-oxothieno[3.2-b]pyridine-6-carboxylic acid and 0.70 g of N, N'-carbonyl diimidazole, followed by agitation under heating at 100° C. for 1 hour. To the resulting solution was added 0.68 g of 1-azabicyclo[2.2.2]oct-3-yl amine dissolved in 4 ml of N, N-dimethylformamide, followed by agitation under heating at 100° C. for 1 hour. After distilling off the solvent under reduced pressure and adding water to the residue, the deposited crystal was filtered, which was then recrystallized in ethanol and water, to obtain 0.73 g of the objective compound.

¹HNMR (CDCl₃, δppm): 1.45–1.60 (1H, m), 1.60–1.80 (2H, m), 1.90–2.10 (2H, m), 2.62–2.75 (1H, m), 2.75–3.07 (4H, m), 3.30–3.50 (1H, m), 3.99 (3H, s), 4.10–4.22 (1H, m), 7.21 (1H, d), 7.84 (1H, d), 8.62 (1H, s), 10.58 (1H, d)

(b) The objective compound (0.70 g) obtained in (a) was dissolved in 10 ml of ethanol, followed by addition of 0.55 ml of the solution of 4N hydrogen chloride in ethyl acetate. After distilling off the solvent, the objective compound (0.78 g) was obtained.

Melting point: 297°–300° C. (decomposed). 2.20–2.42 (2H, m), 3.10–3.12 (1H, m), 3.12–3.42 (4H, m), 3.70–3.83 (1H, m), 4.08 (3H, s), 4.40–4.57 (1H, m), 7.35 (1H, d), 7.98 (1H, d), 8.62 (1H, s), 10.90 (1H, d),

EXAMPLE 10

Synthesis of (endo)-N-(8-methyl-8-azabicyclo[3.2.1]oct-3-yl)-4,7-dihydro-4-methyl-7-oxothieno[3.2-b]pyridine-6-carboxamide (Compound No.4 in Table 1) and hydrochloride thereof (a) To 10 ml of N, N-dimethylformamide were added 0.42 g of 4,7-dihydro-4-methyl-7-oxothieno[3.2-b]pyridine-6-carboxylic acid and 0.39 g of N, N'-carbonyl diimidazole, followed by agitation under heating at 100° C. for 1 hour. To the resulting solution was added 0.23 g of (endo)-8-methyl-8-azabicyclo[3.2.1]oct-3-yl amine dissolved in 2 ml of N, N-dimethylformamide, followed by agitation under heating at 100° C. for 1 hour. After distilling off the solvent under reduced pressure, water was added to the residue. The deposited crystal was filtered, to obtain 0.49 g of the objective compound.

¹HNMR (CDCl₃, δppm): 1.75–1.85 (2H, m), 2.05–2.29 (6H, m), 2.30 (3H, s), 3.10–3.20 (2H, bs), 3.98 (3H, s), 4.22–4.37 (1H, m), 7.19 (1H, d), 7.83 (1H, d), 8.62 (1H, s), 10.60 (1H, d), (b) The objective compound (0.46 g) obtained in (a) was dissolved in 5 ml of chloroform, followed by addition of 0.35 ml of the solution of 4N hydrogen chloride in ethyl acetate. After distilling off the solvent, the objective compound (0.48 g) was obtained.

Melting point: >300° C.,

¹HNMR (CDCl₃, δppm): 2.05–2.15 (2H, m), 2.25–2.42 (2H, m), 2.50–2.62 (2H, m), 2.76 (3H, s ), 2.90–3.10 (2H, m), 3.70–3.80 (2H, bs), 4.01 (3H, s), 4.39–4.52 (1H, m), 7.24 (1H, d), 7.88 (1H, d), 8.64 (1H, s), 10.80 (1H, d)

EXAMPLE 11

Synthesis of N-(1-azabicyclo[2.2.2]oct-3-yl)-7-hydroxy-3-methyl-thieno[3.2-b]pyridine-6-carboxamide (Compound No.10 in Table 2 and its tautomer) and hydrochloride thereof (a) To 26 ml of N, N-dimethylformamide were added 2.00 g of 7-hydroxy-3-methylthieno[3.2-b]pyridine-6-carboxylic acid and 1.70 g of N, N'-carbonyl diimidazole, followed by agitation under heating at 70° C. for 1 hour. To the resulting solution was added 1.45 g of 1-azabicyclo[2.2.2]oct-3-yl amine dissolved in 6 ml of N, N-dimethylformamide, followed by agitation under heating at 65° C. for 2 hours. After distilling off the solvent under reduced pressure, the residue was subjected to silica gel column chromatography (eluent; chloroform:methanol:28% aqueous ammonia=85:15:0.3) for purification, to obtain 2.47 g of the objective compound.

¹HNMR (CDCl₃, δppm): 1.42–1.80 ( 3H, m), 1.90–2.10 ( 2H, m), 2.42 (3H, s), 2.70–3.10 (5H, m), 3.37–3.52 (1H, m), 4.10–4.22 (1H, m), 7.38 (1H, s), 8.75 (1H, s), 10.85 (1H, d), (b) The objective compound (2.00 g) obtained in (a) was dissolved in a mixed solvent of 20 ml of methanol and 20 ml of chloroform, followed by addition of 6.30 ml of the solution of 1N hydrogen chloride in ethanol. After distilling off the solvent, the crystal as the residue was washed in ethanol to obtain the objective compound (1.74 g).

Melting point: 295°–300° C. (decomposed).

¹HNMR (DMSO-d₆, δppm): 1.78–2.15 (4H, m), 2.15–2.30 (1H, m), 2.40 (3H, s), 3.02–3.19 (1H, 3.19–3.50 (4H, m), 3.62–3.80 (1H, m), 4.22–4.40 (1H, m), 7.81 (1H, s), 8.54 (1H, s), 10.68 (1H, d),

EXAMPLE 12

Synthesis of (endo)-N-(8-methyl-8-azabicyclo[3.2.1]oct-3-yl)-7-hydroxy-3-methylthieno[3.2 -b]pyridine-6-carboxamide (Compound No.5 in Table 1 and its tautomer) and hydrochloride thereof (a) To 20 ml of N, N-dimethylformamide were added 2.00 g of 7-hydroxy-3-methylthieno[3.2-b]pyridine-6-carboxylic acid and 1.70 g of N, N'-carbonyl diimidazole, followed by agitation under heating at 70° C. for 1 hour. To the resulting solution was added 1.61 g of (endo)-8-methyl-8-azabicyclo[3.2.1]oct-3-yl amine dissolved in 6 ml of N, N-dimethylformamide, followed by agitation under heating at 65° C. for 2 hours. After distilling off the solvent under reduced pressure, the residue was subjected to silica gel column chromatography (eluent; chloroform:methanol:28% aqueous ammonia=85:15:0.3) for purification, to obtain 3.49 g of the objective compound.

¹HNMR (CDCl₃-CD₃OD, δppm): 1.78–1.90 (2H, m), 2.15–2.30 (6H, m), 2.33 (3H, s), 2.42 (3H, s), 3.20–3.30 (2H, bs), 4.20–4.35 (1H, m), 7.45 (1H, s), 8.57 (1H, s), 10.94 (1H, d), (b) The objective compound (2.00 g) obtained in (a) was dissolved in a mixed solvent of 25 ml of chloroform and 25 ml of methanol, followed by addition of 6.03 ml of the solution of 1N hydrogen chloride in ethanol. After distilling off the solvent and washing the residue in ethanol, the objective compound (2.06 g) was obtained.

Melting point: >300° C.

¹HNMR (DMSO-d₆, δppm): 1.85–2.10 (2H, m), 2.20–2.35 (4H, m), 2.40 (3H, s), 2.50–2.65 (2H, m), 2.69 (3H, 3.80–3.95 (2H, bs), 4.10–4.23 (1H, m), 7.81 (1H, s), 8.53 (1H, s), 10.84 (1H, d)

EXAMPLE 13

Synthesis of N-(1-azabicyclo[2.2.2]oct-3-yl)-7-hydroxy-3-methyl-thieno[3.2-b]pyridine-6-carboxamide (Compound No.11 and tautomer in Table 2) and hydrochloride thereof (a) To 10 ml of N, N-dimethylformamide were added 0.29 g of 7-hydroxy-2-methylthieno[3.2-b]pyridine-6-carboxylic acid and 0.50 g of N, N'-carbonyl diimidazole, followed by agitation under heating at 90° C. for 1.5 hours. To the resulting solution was added 0.42 g of 1-azabicyclo[2.2.2]oct-3-yl amine dissolved in 4 ml of N, N-dimethylformamide, followed by agitation under heating at 75° C. for 7 hours. After distilling off the solvent under reduced pressure, the residue was subjected to silica gel column chromatography (eluent; chloroform:methanol:28% aqueous ammonia=85:15:0.3) for purification, to obtain 0.32 g of the objective compound.

¹HNMR (CDCl₃-CD₃OD, δppm): 1.58–1.72 (1H, m), 1.72–1.95 (2H, m), 1.95–2.12 (2H, m), 2.63 (3H, s), 2.65–2.80 (1H, m), 2.82–3.10 (4H, m), 3.35–3.50 (1H, m), 4.12–4.22 (1H, m), 6.91 (1H, s), 8.56 (1H, s), 10.89 (1H, d), (b) The objective compound (0.32 g) obtained in (a) was dissolved in ethanol, followed by addition of 1.01 ml of the solution of 1N hydrogen chloride in ethanol. After distilling off the solvent, the resulting crystal was washed in ethanol to obtain 0.21 g of the objective compound.

Melting point: 298°–300° C. (decomposed).

¹HNMR (DMSO-d₆, δppm): 1.80–2.16 (4H, m), 2.16–2.22 (1H, m), 2.59 (3H, s), 3.00–3.16 (1H, m), 3.16–3.38 (4H, m), 3.62–3.80 (1H, m) 4.22–4.38 (1H, m), 7.15 (1H, s), 8.58 (1H, s), 10.35–10.50 (1H, bs), 10.70 (1H, d)

EXAMPLE 14

Synthesis of N-(1-azabicyclo[2.2.2]oct-3-yl)-3-bromo-7-hydroxy-thieno[3.2-b]pyridine-6-carboxamid (Compound No.12 and tautomer in Table 2) and hydrochloride thereof (a) To 5 ml of N, N-dimethylformamide were added 0.15 g of 3-bromo-7-hydroxythieno[3.2-b]pyridine-6-carboxylic acid and 0.09 g of N, N'-carbonyl diimidazole, followed by agitation under heating at 80° C. for 1 hour. To the resulting solution was added 0.80 g of 1-azabicyclo[2.2.2]oct-3-yl amine dissolved in 2 ml of N, N-dimethylformamide, followed by agitation under heating at 80° C. for 2 hours. After distilling off the solvent under reduced pressure, the residue was subjected to silica gel column chromatography (eluent; chloroform:methanol:28% aqueous ammonia=85:15:0.3) for purification, to obtain 0.14 g of the objective compound.

(b) The objective compound (0.14 g) obtained in (a) was dissolved in a mixed solvent of 20 ml of ethanol and 20 ml of chloroform, followed by addition of 0.37 ml of the solution of 1N hydrogen chloride in ethanol. After distilling off the solvent, the resulting crystal was washed in ethanol to obtain the objective compound (0.11 g).

Melting point: >300° C.,

¹HNMR (DMSO-d₆, δppm): 1.80–2.10 (4H, m), 2.10–2.22 (1H, m), 3.00–3.15 (1H, m), 3.15–3.30 (4H, m), 3.60–3.75 (1H, m), 4.25–4.40 (1H, m), 8.37 (1H, s), 8.54 (1H, s), 10.45 (1H, d)

EXAMPLE 15

Synthesis of (endo)-N-(8-methyl-8-azabicyclo[3.2.1]oct-3-yl)-3-bromo-7-hydroxythieno[3.2-b]pyridine-6-carboxamide (Compound No.6 in Table 1 and its tautomer) and hydrochloride thereof (a) To 5 ml of N, N-dimethylformamide were added 0.17 g of 3-bromo-7-hydroxythieno[3.2-b]pyridine-6-carboxylic acid and 0.11 g of N, N'-carbonyl diimidazole, followed by agitation under heating at 90° C. for 1 hour. To the resulting solution was added 0.06 g of (endo)-8-methyl-8-azabicyclo[3.2.1]oct-3-yl amine dissolved in 4 ml of N, N-dimethylformamide, followed by agitation under heating at 80° C. for 2 hours. After distilling off the solvent under reduced pressure, the residue was subjected to silica gel column chromatography (eluent; chloroform:methanol:28% aqueous ammonia=85:15:0.3) for purification, to obtain 0.11 g of the objective compound.

(b) The objective compound (0.11 g) obtained in (a) was dissolved in a mixed solvent of 2 ml of ethanol and 2 ml of chloroform, followed by addition of 0.3 ml of the solution of 1N hydrogen chloride in ethanol. After distilling off the solvent, the resulting crystal was washed in ethanol, to obtain the objective compound (0.10 g).

Melting point: >300° C.,

¹HNMR (DMSO-d₆, δppm): 1.90–2.10 (2H, m), 2.20–2.42 (4H, m), 2.42–2.60 (2H, m), 2.68 (3H, s), 3.80–3.95 (2H, bs), 4.12–4.25 (1H, m), 8.40 (1H, s), 8.35 (1H, s), 10.20–10.40 (1H, b), 10.63 (1H, d), Benzamide derivatives such as metoclopramide (see, for example, Merck Index, 11 eds., 6063(1989)), cisapride (see Japanese Patent Laid-open No. Sho 58-90552), BRL-24924 (see Japanese Patent Laid-open No. Sho 62-270583), etc. have been known as a compounds enhancing gastric motor action. The compound of the present invention are a compound having strong action to enhance gastric motor action and having a totally different structure from those of the above compounds.

As will be described hereinbelow, the compound of the present invention inhibits the temporary bradycardia via serotonin in a male Wistar rat under anesthesia, which indicates that the compounds have also the antagonistic activity of 5-HT3 (serotonin 3) receptor as will be observed in BRL-24924. Therefore, the generally known effect via the 5-HT3 receptor antagonistic activity (Japanese Patent Laid-open No. Sho 62-270583, Japanese Patent Laid-open No. Hei 2-237920, Japanese Patent Laid-open No. Hei 3-223278) will be expected from the compounds. Thus, the compounds are believed to have efficacy on the prevention and therapeutical treatment of hypersensitive colon syndrome, vomiting and nausea due to anti-tumor agents and radiation, migraine headache, complex headache, prosopalgia, peripheral ache, nervous symptoms, neurosis, and arrhythmia.

The pharmacological effect of the compounds of the present invention has been confirmed as follows.

Test Example 1

Promoting action of mouse gastric emptying

Male, ddy mice (body weight; 20 to 25 g) were used. 24-Hour after starvation 1 mg/kg test compounds dissolved in distilled water were orally administered (10 ml/kg). To the control group distilled water was orally administered (10 ml/kg). One hour later, a 2000 ppm phenol red solution (suspended in aqueous 0.5% carboxymethyl cellulose solution) was administered to each mouse (liquid dose; 0.05 ml/mouse). Then, 15 minutes later, the animals were killed to remove the stomachs. The phenol red retained in the stomachs was developed in 20 ml of a 2.75% trisodium phosphate solution, and analyzed with an absorption photometer at a wave length of 540 nm (A). Immediately after the phenol red solution was administered, the animals were killed to quantitatively determine the phenol red left in the stomachs (B). The difference in the amount of phenol red between A and B (B-A) was designated as gastric emptying. The gastric emptying of the test compounds were shown in Table 4 below, provided that the gastric emptying of the control group was defined as 100%.

TABLE 4

| Test Compound | Promoting Action of Gastric Emptying (%) 1 mg/kg, p.o. |
|---|---|
| Example 1 | 147 |
| Example 2 | 185 |
| Example 10 | 140 |
| Example 11 | 152 |

Example 1

2) Promoting action of dog gastric contraction

An implant-type strain-gauge transducer was sutured onto the serosa at the autrum (about 3 cm above pylorus) of adult mongrel dogs, weighed 11 to 15 kg, so as to determine the contraction of the circular muscle. Two weeks or more after the surgery, the gastric contraction was recorded for analysis with a data processing device. In the state of starvation, an interdigestive migrating contraction (abbreviated as IMC hereinbelow) occurring at a cycle of about 90 minutes and continuing for about 20 minutes was observed at the autrum. The dog was put to starvation for about 16 hours. Ten minutes after the completion of one IMC, a test compound was intravenously administered. The contraction for the 30-minute interval thereafter was represented as a percentage (%) to the IMC contraction having occurred immediately before, and the dose developing the 50% contraction was defined as $ED_{50}$.

The results are shown in Table 5.

TABLE 5

| Test Compound | $ED_{50}$ (mg/kg, i.v.) |
|---|---|
| Example 1 | 0.01 |
| Example 2 | 0.005 |
| BRL-24924 | 0.1 |

3) 5-HT$_3$ antagonistic action (antagonistic action of Bezold-Jarish reflex)

According to the following method, the assessment of a compound in terms of the antagonistic action of Bezold-Jarish reflex triggered by 5-HT was carried out in a rat under anesthesia.

A male Wistar rat, weighed 300 to 400 g, was anesthetized with an intra-parenteral dose of 1.2 g/kg urethane, to monitor the heart rate triggered by electrocardiography. Five minutes after saline was intravenously administered (0.5 ml/kg) to the rat, 5-HT (8 μg/kg) dissolved in saline (0.5 ml/kg) was intravenously administered firstly, to measure the change in cardiac output (A). To the same rat after 10 minutes interval, the test compound was intravenously administered, 5 minutes later 5-HT was administered in the same fashion, to measure the change in heart rate (B). Based on these values, the inhibition ratio of the test compound was calculated by the following formula:

Calculation formula:

$$\text{inhibition ratio} = (1 - B/A) \times 100$$

Also, the dose with the inhibition ratio of 50% was defined as the $ID_{50}$ of the test compound.

The results are shown in Table 6.

TABLE 6

| Compound | $ID_{50}$ (μg/kg, i.v.) |
|---|---|
| Example 1 | 0.15 |
| Example 2 | 0.02 |

For the test of acute toxicity, male ddy mice (body weight; 25 to 30 g, 3 mice for one test compound) were used. Test compound of Example 1 or 2 was orally administered at 1000 mg/kg. The rats were put under observation for 7 days after the dosage, but with no death, which indicates that acute toxicity of the compounds of the present invention is low.

What we claim is:

1. A thieno[3,2-b]pyridine derivative represented by formula (I):

wherein Y represents —O— or $$-\underset{\underset{R^1}{|}}{N}-$$

(wherein $R^3$ represents hydrogen atom or a $C_1$–$C_6$ alkyl group); $R^1$ represents hydrogen atom, a $C_1$–$C_6$ alkyl group, a $C_2$–$C_6$ alkenyl group, a $C_2$–$C_6$ alkynyl group, a $C_3$–$C_8$ cycloalkyl group, a $C_6$–$C_{12}$ aryl group, or a $C_7$–$C_{18}$ aralkyl group; $R^2$ represents hydrogen atom, a $C_1$–$C_6$ alkyl group, halogen atom, hydroxyl group, a $C_1$–$C_6$ alkoxyl group, amino group, a $C_1$–$C_6$ alkylamino group, nitro group, mercapto group or a $C_1$–$C_6$ alkylthio group; and A is represented by

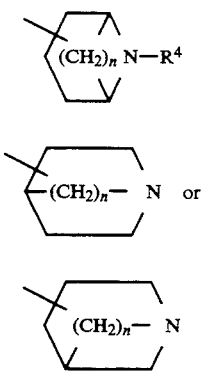

(wherein n is an integer of 1 to 4; $R^4$ represents hydrogen atom, a $C_1$-$C_6$ alkyl group, a $C_3$-$C_8$ cycloalkyl group or a $C_7$-$C_{18}$ aralkyl group); a pharmaceutically acceptable salt thereof; an N-oxide derivative or a solvate thereof.

2. A compound according to claim 1, wherein Y represents —O— or

(wherein $R^3$ represents hydrogen atom); $R^1$ represents hydrogen atom, a $C_1$-$C_6$ alkyl group, a $C_6$-$C_{12}$ aryl group or a $C_7$-$C_{18}$ aralkyl group; $R^2$ represents hydrogen atom, a $C_1$-$C_6$ alkyl group, or halogen atom; and A is represented by

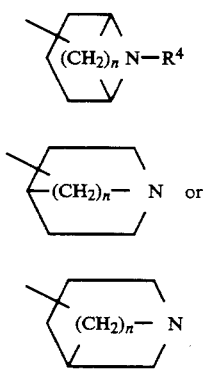

(wherein n is an integer of 2 or 3; $R^4$ represents a $C_1$-$C_6$ alkyl group).

3. A compound according to claim 2, wherein $R^1$ represents hydrogen atom or a $C_1$-$C_3$ alkyl group; $R^2$ represents hydrogen atom, a $C_1$-$C_3$ alkyl group or halogen atom; and A is represented by

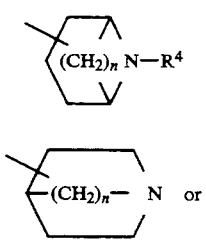

(wherein n is an integer of 2 or 3; $R^4$ represents a $C_1$-$C_3$ alkyl group).

4. A pharmaceutical composition containing a substance according to claim 1 and a pharmaceutically acceptable carrier.

5. A pharmaceutical composition for preventing and therapeutically treating the diseases caused by gastrointestinal dismotility, containing a substance according to claim 1 as the effective ingredient and a pharmaceutically acceptable carrier.

6. A pharmaceutical composition for preventing and therapeutically treating vomiting and/or nausea, containing a substance according to claim 1 as the effective ingredient and a pharmaceutically acceptable carrier.

7. An analgesic composition containing a substance according to claim 1 as the effective ingredient and a pharmaceutically acceptable carrier.

8. A pharmaceutical composition for preventing and therapeutically treating anxiety and/or neurosis, containing a substance according to claim 1 as the effective ingredient and a pharmaceutically acceptable carrier.

9. A pharmaceutical composition for preventing and therapeutically treating arrhythmia, containing a substance according to claim 1 as the effective ingredient and a pharmaceutically acceptable carrier.

10. A thieno[3,2-b]pyridine derivative represented by formula (Ib'), a pharmaceutically acceptable salt thereof, an N-oxide derivative thereof or a solvate thereof;

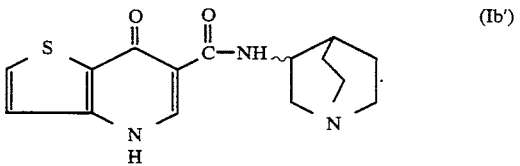

11. A compound according to claim 11, in the form of an optical isomer which has the R-configuration.

12. R-N-(1-azabicyclo[2.2.2]oct-3-yl)-7-hydroxythieno[3,2-b]pyridine-6-carboxamide hydrochloride.

13. A pharmaceutical composition containing a substance according to claim 10, and a pharmaceutically acceptable carrier.

14. A pharmaceutical composition containing a substance according to claim 11, and a pharmaceutically acceptable carrier.

15. A pharmaceutical composition containing a substance according to claim 12, and a pharmaceutically acceptable carrier.

16. A pharmaceutical composition for preventing and treating the disease caused by gastrointestinal dismotility, containing a substance according to claim 10, as the effective ingredient and a pharmaceutically acceptable carrier.

17. A pharmaceutical composition for preventing and treating the disease caused by gastrointestinal dismotility, containing a substance according to claim 11, as the effective ingredient and a pharmaceutically acceptable carrier.

18. A pharmaceutical composition for preventing and treating the disease caused by gastrointestinal dismotility, containing a substance according to claim 12, as the effective ingredient and a pharmaceutically acceptable carrier.

19. A method of preventing and treating the disease caused by gastrointestinal dismotility, which comprises administering to a patient an effective amount of a compound claimed in claim 10.

20. A method of preventing and treating the disease caused by gastrointestinal dismotility, which comprises administering to a patient an effective amount of a compound claimed in claim 11.

21. A method of preventing and treating the disease caused by gastrointestinal dismotility, which comprises administering to a patient an effective amount of a compound claimed in claim 12.

* * * * *